United States Patent [19]
Burzynski

[11] Patent Number: 6,127,419
[45] Date of Patent: Oct. 3, 2000

[54] PHENYLACETIC ACID COMPOSITIONS FOR TREATING OR PREVENTING ATHEROSCLEROSIS AND RESTENOSIS

[76] Inventor: Stanislaw R. Burzynski, 20 W. Rivercrest, Houston, Tex. 77042

[21] Appl. No.: 09/197,903

[22] Filed: Nov. 23, 1998

[51] Int. Cl.[7] .......................... A01N 37/12; A01N 31/08
[52] U.S. Cl. ...................... 514/563; 514/731; 514/732
[58] Field of Search ..................... 514/532, 544, 514/561, 731, 732, 563

[56] References Cited

U.S. PATENT DOCUMENTS

| | | | |
|---|---|---|---|
| 4,470,970 | 9/1984 | Burzynski | 424/177 |
| 5,387,601 | 2/1995 | Hill | 514/397 |
| 5,605,930 | 2/1997 | Samid | 514/510 |
| 5,705,507 | 1/1998 | Muehl | 514/320 |

OTHER PUBLICATIONS

Indolfi, et al., "Smooth Muscle Cell Proliferation Is Proportional to the Degree of Balloon Injury in a Rat Model of Angioplasty," *Circulation* 92:1230–1235 (1995).

Guijarro, et al., "3–Hydroxy–3–Methylglutaryl Coenzyme A Reductase and Isoprenylation Inhibitors Induce Apoptosis of Vascular Smooth Muscle Cells in Culture," *Circulation Research* 83:490–500 (Sep. 1998).

*Primary Examiner*—Theodore J. Criares
*Attorney, Agent, or Firm*—Howrey Simon Arnold & White, LLP

[57] ABSTRACT

Pharmaceutical compositions effective in treating or preventing atherosclerosis and restenosis are disclosed. The pharmaceutical compositions of the present invention comprise one or more compounds selected from the group consisting of phenylacetic acid, pharmaceutically-acceptable salts thereof, pharmaceutically-acceptable precursors thereof, and pharmaceutically-acceptable analogs thereof (e.g., phenylacetylglutamine and isophenylacetylglutamine), suitably combined with appropriate carriers, diluents, or excipients. The compositions also optionally contain isoglutamine. Also disclosed are methods for treating or preventing atherosclerosis and restenosis by the administration of pharmaceutical compositions of the present invention.

9 Claims, No Drawings

PHENYLACETIC ACID COMPOSITIONS FOR TREATING OR PREVENTING ATHEROSCLEROSIS AND RESTENOSIS

BACKGROUND OF THE INVENTION

1. Field of the Invention

The present invention relates generally to the fields of pharmaceutical chemistry. More particularly, it concerns the use of an effective amount of phenylacetic acid, pharmaceutically-acceptable salts thereof, precursors thereof, or analogs thereof, singly or in any combination, and optionally also isoglutamine, in the treatment and prevention of atherosclerosis and restenosis.

2. Description of Related Art

In the United States, roughly 500,000 people die from coronary heart disease and 750,000 suffer heart attacks every year. Thousands more also die of stroke. A major cause of heart disease, heart attack, and stroke is atherosclerosis. Atherosclerosis is the growth of lesions on the walls of the aorta and other arteries, and its asymptomatic early stages are ubiquitous in populations with high-caloric, fat-rich diets such as are common in the United States and Europe. In its advanced stages, atherosclerotic lesions, commonly termed plaques, lead to constriction of the arterial lumen, resulting in impaired oxygen flow to the heart (angina) and the potential for thrombosis (blockage of blood flow by the presence of a clot), which may cause a heart attack or stroke.

Atherosclerotic lesions originate in the lining (intima) or middle layer (media) of the aorta and other arteries, as a focal overgrowth of smooth muscle cells. Recent investigations have uncovered evidence that a lesion may be a monoclonal overgrowth of smooth muscle cells. In other words, a lesion may correspond to a benign smooth muscle tumor. Although detailed understanding of this phenomenon remains the subject of inquiry, it has recently been postulated that smooth muscle cell proliferation may be caused, at least in part, by inactivation of the tumor suppressor gene p53.

Currently, factors that increase the risk of atherosclerosis are fairly well known. These factors include diets high in saturated fats and cholesterol, smoking, obesity, and conditions such as diabetes. Elimination or minimization of these risk factors has value in slowing the advancement of atherosclerosis. However, in the treatment of advanced atherosclerosis, more drastic and invasive procedures may be required. Coronary bypass operations involve grafting a blood vessel from a different pair of the body, typically a vein from a leg, into the arterial vasculature of the heart to circumvent a region severely occluded by atherosclerotic plaques. Unfortunately, a coronary bypass is a major surgical procedure, requiring opening of the chest and cardiopulmonary support.

A less invasive procedure is angioplasty, most commonly, balloon angioplasty. In angioplasty, a catheter with a deflated balloon at the end is inserted into the patient's vasculature. When a region of severe atherosclerotic plaques is found, the balloon is inflated in order to crush the lesions against the arterial wall. According to a recent estimate, approximately 330,000 patients undergo coronary angioplasty in the United States every year (Science 265, 320 (1994)). However, not even angioplasty is without shortcomings, as the occlusion of the arterial lumen during inflation of the balloon may block blood flow to the heart or brain and produce a heart attack or stroke. Also, atherosclerotic plaques may mask weak spots in the arterial wall, and balloon inflation may overstress the weak spots and lead to hemorrhage.

Therefore, it is desirable to have non-invasive methods of preventing atherosclerotic plaque formation and treating atherosclerotic plaques once formed. It is desirable for such methods to comprise administration of a pharmaceutical composition effective in inhibiting plaque formation or activating plaque degradation, such pharmaceutical composition having minimal toxicity and as few undesirable side effects as possible.

In addition to the above-listed shortcomings of coronary by pass and angioplasty procedures, on occasion after treatment, the artery becomes reoccluded. This reocclusion is termed "restenosis." The net result of restenosis is a return to conditions of impaired blood flow to the heart or brain, with an attendant risk for angina, heart attack, or stroke.

Restenosis occurs in roughly one-third of angioplasty patients within one to six months after angioplasty, and will inevitably occur in the grafted venous tissue of coronary bypass patients, though over longer time frames. Although the detailed physiology of restenosis has not yet been elucidated, it is known to involve the excessive proliferation of smooth muscle cells in arterial walls, and is believed to be caused by the same processes that give rise to atherosclerosis.

At present, the leading technique for treating or preventing restenosis is the use of stents to mechanically hold open the arterial lumen. Drawbacks of the use of stents include the invasiveness of insertion.

Therefore, it is desirable to have non-invasive methods of preventing and treating restenosis. It is desirable for such methods to comprise administration of a pharmaceutical composition effective in inhibiting restenosis, such pharmaceutical composition having minimal toxicity and as few undesirable side effects as possible.

It has been known for some time that compounds such as 3-phenylacetylamino-2,6-piperidinedione and its hydrolysis products, such as phenylacetic acid, and salts and analogs thereof (together, "3-phenylacetylamino-2,6-piperidinedione and its derivatives"), play roles in the inhibition of tumor growth and the differentiation of malignant dedifferentiated cells. The implication of the tumor-suppressor gene p53 in proliferation of smooth muscle cells, and the role of smooth muscle cells in atherosclerotic plaque formation and restenosis, indicated that antitumor agents merited examination for use in treating or preventing atherosclerosis and restenosis. Therefore, it was desirable to determine which, if any, of 3-phenylacetylamino-2,6-piperidinedione and its derivatives may inhibit smooth muscle cell proliferation, and thus may form the basis of a pharmaceutical composition useful in treating or presenting atherosclerosis and restenosis. Derivatives of 3-phenylacetylamino-2,6-piperidinedione that exhibit such inhibition are disclosed herein.

SUMMARY OF THE INVENTION

In one aspect, the present invent ion includes a method for the treatment or prevention of atherosclerosis and restenosis comprising the step of administering a pharmaceutical composition comprising a therapeutically-effective amount of phenylacetic acid, a pharmaceutically-acceptable salt thereof, a pharmaceutically-acceptable precursor thereof, or a pharmaceutically-acceptable analog thereof, and optionally also isoglutamine, with a pharmaceutically-acceptable carrier, diluent, or excipient, to a patient. The patient may have confirmed atherosclerosis, in which case the administration of the pharmaceutical composition is intended to treat the condition, or be asymptomatic or at risk for atherosclerosis due to diet, smoking, body weight, age, sex, family history, or other condition, in which case the administration of the pharmaceutical composition is intended as a prophylactic measure to prevent advanced stage atherosclerosis and its sequelae such as angina, heart attack, or stroke.

The patient may have confirmed restenosis, in which case the administration of the pharmaceutical composition is intended to treat the condition, or the patient may have undergone angioplasty or coronary bypass but not yet been confirmed to have restenosis, in which case the administration of the pharmaceutical composition is intended to prevent the occurrence of the condition and its sequelae.

Alternatively, the pharmaceutical composition comprises therapeutically-effective amounts of two or more compounds, each compound selected from the group consisting of phenylacetic acid, pharmaceutically-acceptable salts thereof, pharmaceutically-acceptable precursors thereof, and pharmaceutically-acceptable analogs thereof, and optionally also isoglutamine, with a pharmaceutically-acceptable carrier, diluent, or excipient.

In a second aspect, the invention includes a pharmaceutical composition for the treatment or prevention of atherosclerosis or restenosis, comprising a therapeutically-effective amount of phenylacetic acid, a pharmaceutically-acceptable salt thereof, a pharmaceutically-acceptable precursor thereof, or a pharmaceutically-acceptable analogs thereof, and optionally also isoglutamine, with a pharmaceutically-acceptable carrier, diluent, or excipient. Alternatively, the pharmaceutical composition comprises therapeutically-effective amounts of two or more compounds, each compound selected from the group consisting of phenylacetic acid, pharmaceutically-acceptable salts thereof, pharmaceutically-acceptable precursors thereof, and pharmaceutically-acceptable analogs thereof, and optionally also isoglutamine, with a pharmaceutically-acceptable carrier, diluent, or excipient.

DETAILED DESCRIPTION OF EMBODIMENTS

The invention is described below in terms of preferred embodiments known at the time of filing of this application. These embodiments represent the best mode presently contemplated for preparing the pharmaceutical compositions and their method of use.

A. Preparation of pharmaceutical compositions

Phenylacetic acid, used in the present compositions, either directly or as a salt or analog, can be extracted from natural body fluids or can be prepared synthetically by any technique known in the art, e.g. by the acid hydrolysis of phenylacetylglutamic acid or by the oxidation of β-phenethyl alcohol with dichromate or permanganate. For pharmaceutical use, phenylacetic acid is preferably prepared synthetically. The structural formula for phenylacetic acid is as follows:

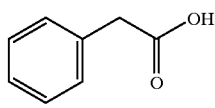

Analogs of phenylacetic acid that can be used in the present invention include:

phenylacetylglutamine

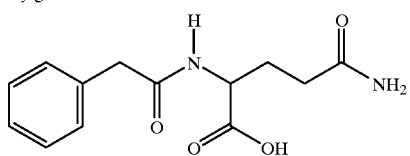

iso-phenylacetylglutamine

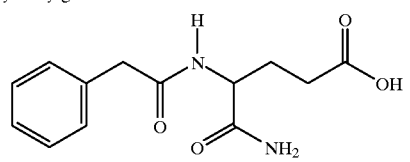

and those of Formula I:

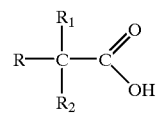

wherein R and $R_1$ are independently selected from the group consisting of H, lower alkoxy, or lower alkyl; and $R_2$ is selected from the group consisting of aryl and substituted aryl. Preferably, R is selected from the group consisting of H and $C_3H_7$; $R_1$ is selected from the group consisting of H, $CH_3$, $CH_3$—O—, $C_2H_5$, and $C_3H_7$; and $R_2$ is selected from the group consisting of (Formula II):

Formula II

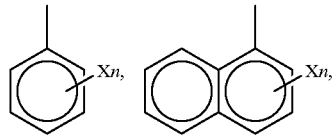

wherein X is a methyl, halogen or hydroxy and n is 0, 1, 2, 3, or 4. More preferably, $R_2$ is a phenyl group or selected from the group of Formula II, wherein X is selected from Cl, F, or OH. Most preferably, $R_2$ is selected from the group of Formula II, wherein X is Cl. All such analogs of phenylacetic acid can be synthesized by techniques known to those skilled in the art. Pharmaceutically-acceptable analogs of phenylacetic acid are those having the biological activity of the parent compound and lacking toxic activity at the selected administration level. Determination of whether an analog is pharmaceutically-acceptable can be accomplished by methods known to those of skill in the art.

The compounds of the present invention can also exist in different stereoisomeric forms by virtue of the presence of one or more asymmetric centers in the compound. The present invention contemplates all stereoisomeric forms of the compounds as well as mixtures thereof, including racemic mixtures. Individual stereoisomers may be obtained, if desired, by methods known in the art as, for example, the separation of stereoisomers in chiral chromatographic columns.

"Pharmaceutically-acceptable salts" means salts having the biological activity of the parent compound and lacking toxic activity at the selected administration level. Again, determination of whether a salt is pharmaceutically-acceptable can be accomplished by methods known to those of skill in the art. Pharmaceutically-acceptable salts include, but are not limited to, inorganic sodium, potassium and ammonium salts, and organic diethanolamine, cyclohexylamine, and amino acid salts. Preferably, the salt is an alkali or alkaline earth metal salt. More preferably, the salt is an alkali metal salt. Most preferably, the salt is a sodium salt.

Precursors of phenylacetic acid can be used in the present compositions. Precursors of phenylacetic acid are hereby defined herein as compounds that can be metabolized to yield phenylacetic acid in humans. Pharmaceutically-acceptable precursors of phenylacetic acid are precursors which lack toxic activity at the selected administration level, either per se or as any metabolic intermediate between the precursor and phenylacetic acid. Determination of whether precursors of phenylacetic acid are pharmaceutically acceptable can be achieved by application of methods known to those of skill in the art. A preferred precursor of phenylacetic acid for use in the present invention is phenylbutyrate. The structural formula of phenylbutyrate is as follows:

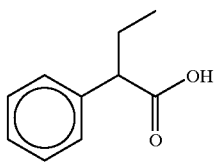

Together, salts, precursors, and analogs of phenylacetic acid may be referred to herein as compounds related to phenylacetic acid, or simply "related compounds."

Isoglutamine can optionally be used in the present compositions. Isoglutamine can be extracted from natural body fluids or can be prepared synthetically by acid hydrolysis of phenylacetylisoglutamic acid. The structural formula of isoglutamine is:

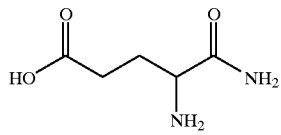

One or more compounds selected from the group consisting of phenylacetic acid, salts thereof, precursors thereof, and analogs thereof, and optionally isoglutamine, are then combined with an appropriate carrier, diluent, or excipient to prepare a pharmaceutical composition for administration to a patient. The composition should comprise an effective amount of the one or more compounds selected from the group consisting of phenylacetic acid, salts thereof, precursors thereof, and analogs thereof, and optionally isoglutamine, used therein. An "effective amount" of a compound of the present invention is an amount capable of alleviating or preventing atherosclerosis or restenosis. The effective amount of a compound in a pharmaceutical composition of the present invention will be determined by a combination of parameters, including, but not limited to, the compound administered, the route of administration, the dose rate, and the condition of the patient.

Typical daily doses of the compounds of the present invention will be in the range of from about one (1) mg/kg/d (low) to 400 mg/kg/d (high). Preferred daily doses will generally be in the range of 100 mg/kg/d.

The composition can be prepared for administration via a variety of routes, including oral, rectal, transdermal, subcutaneous, intravenous, intramuscular, and intranasal. Preferably, the route of administration will be oral, rectal, or intravenous.

Pharmaceutical compositions of the present invention can be prepared using techniques and ingredients known to those skilled in the art, examples of which are given in the following paragraphs. One or more ingredients, other than phenylacetic acid and related compounds, may be present as carriers, diluents, or excipients in any composition of the present invention.

Ingredients that can be used as carriers, diluents, or excipients in the present invention include, but are not limited to, solvents such as water, alcohol, ether, glycerin, oils, and soaps; ointment bases such as hard, soft, or liquid paraffin; emulsifiers such as lanolin, petrolatum, bentonite, magnesium aluminum silicate, gelatin, acacia, methylcellulose, pectin, tragacanth, sodium lauryl sulfate, benzalkonium chloride, and polyethylene glycol 400 monostearate; aqueous gel formers such as acacia, cellulose, chondrus, gelatin, gelatinized starch, and tragacanth; and paste formers such as glycogelatin, paraffin, and starch.

For solid compositions, ingredients that can be used as carriers, diluents, or excipients include, but are not limited to, encapsulants such as hard gelatin or soft gelatin; diluents such as dextrin, lactose, salt, and starch; lubricants such as liquid paraffin, stearic acid, and talc; coatings such as sucrose syrup, starch suspensions, calcium carbonate, magnesium carbonate, cellulose and cellulose derivatives, including cellulose acetate phthalate; lozenge formers such as sugar, gum, and gelatin; and suppository formers such as theobroma oil.

If the composition is intended for oral administration, it can be formulated as a tablet, capsule, powder, spirit, or elixir, among others. If the composition is intended for rectal administration, it can be formulated as a suppository. If the composition is intended for intravenous administration, it can be formulated as an intravenous solution of sodium salts in water for injection.

B. Method of Administration of Pharmaceutical Compositions

A pharmaceutical composition of the present invention can be administered via whatever route is appropriate for its formulation described above. If the composition is formulated as a tablet or capsule, 1–5 tablets or capsules each containing 1–1000 mg of phenylacetic acid or related compound can be administered orally 1–8 times per day. If formulated as a powder or elixir, 5–50 ml of elixir or solvent containing 1–1000 mg of phenylacetic acid or related compound can be administered orally 1.8 times per day.

If formulated as a suppository, one suppository containing 1–1000 mg of phenylacetic acid or related compound can be administered rectally 1–8 times per day.

If formulated as an intravenous solution, 1 mL to 4 mL of solution containing 1 to 300 mg of phenylacetic acid or related compound can be administered per minute for a period of 0.25 min (15 sec) to 240 min, 1–96 times per day. For example, one type of IV administration may include from 0.25 mL to 30 mL every 15 min (96× a day) at 4 mL/min. Another type of administration may include from 5 mL to 500 mL at 1 mL/hr to 250 ml/hr every 4 hours. Finally, it can be administered continuously from 1 mL/hr to 250 mL/hr. Two formulations used for treatment of cancer were named Antineoplaston A10 ("A10") and Antineoplaston AS2-1 ("AS2-1"). A10 consists essentially of sodium salts of phenylacetylglutamine and isophenylacetylglutamine in a 4:1 ratio, and AS2-1 consists essentially of sodium salts of phenylacetylglutamine and phenylacetic acid in a 1:4 ratio. The highest concentration of A10 for IV administration is 300 mg/mL and for AS2-1 150 mg/ml. A10 and AS2-1 can be administered up to a concentration of 100 mg/mL intraarterially from 1 mL/hr to 100 mL/hr.

The duration of the therapeutic regimen may be for only so much time as is required for alleviation of atherosclerosis or restenosis, if phenylacetic acid or a related compound is administered for treatment of the condition. Alternatively, if phenylacetic acid or a related compound is administered as a prophylactic to prevent the occurrence of restenosis or atherosclerosis, the duration of the therapeutic regimen may be for any or all of the 0–6 months following angioplasty, or for any or all of the length of time following coronary bypass, or, if administered to prevent atherosclerosis, for any or all of the patient's lifespan remaining after the commencement of treatment.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Inhibition of DNA synthesis in smooth muscle cells by phenyl acetic acid and a related compound in vitro A composition comprising sodium salts of phenylacetylglutamine:phenylacetic acid in a 1:4 ratio, hereinafter referred to as AS2-1, was tested for its ability to inhibit DNA synthesis in smooth muscle cells in vitro. These results indicated that AS2-1 was capable of inhibiting DNA synthesis in smooth muscle cells, and would thus inhibit proliferation of smooth muscle cells.

Test samples of rat smooth muscle cells were treated with AS2-1 (1–4 mg/mL), whereas control samples were treated in an identical manner with a formulation identical to the test treatment with the exception that no AS2-1 was present. DNA synthesis was measured by extraction of DNA from an equal number of cells of both test and control samples taken both before and after treatment. Cell counts were performed by cytometry. Extracted DNA was quantitated by absorbance of aqueous solutions at 260 nm or intensity of ethidium bromide staining of electrophoretic separation. All experiments were repeated at least in triplicate.

Control samples yielded an increasing amount of DNA over time which correlated directly with the number of cells present. This indicated that the control samples continued to grow at an expected rate. The test samples, however, yielded DNA levels that were significantly reduced relative to the control samples. Furthermore, the number of smooth muscle cells scored by visual inspection and cytometry did not increase during the treatment regimen. These results indicate that AS2-1 can inhibit DNA synthesis and normal cellular proliferation of rat smooth muscle cells.

The results of the in vitro smooth muscle cell DNA synthesis test indicate that pharmaceutical formulations of phenylacetic acid and related compounds can inhibit smooth muscle cell proliferation in vivo. This conclusion was verified in further experiments.

EXAMPLE 2

Inhibition of DNA synthesis by rat smooth muscle cells in vivo

A composition comprising AS2-1 was tested for its ability to inhibit DNA synthesis in smooth muscle cells in vivo. These experiments were performed in a rat model system in which restenosis was encouraged by injury to smooth muscle cells of the carotid artery by means of angioplasty balloons. These results indicated that AS2-1 was capable of inhibiting DNA synthesis in smooth muscle cells in vivo.

Rats were divided into three groups: test, angioplasty-control, and control. The test and angioplasty-control rats received angioplasty of the carotid artery. Injury to the arterial wall was performed using an angioplasty balloon. Control rats received no angioplasty. Rats of all three groups were returned to cages under identical regimens of food, water, temperature, light/dark cycle, etc .

Rats in the test group received AS2-1 by oral administration, 250 mg/kg twice per day for 14 d. Rats in the angioplasty-control and control groups received placebo of identical size. At the end of the 14 d period, rats in all three groups were sacrificed and the carotid arteries were rapidly dissected and cut into lengths of 0.5 cm. Smooth muscle cells from each length of carotid artery were isolated. The DNA was extracted from the cells and quantified substantially as described in Example 1 above. Given the identical lengths and very similar diameters of the carotid arteries of the rats of all three groups, DNA quantities for this example will be reported as $\mu$g/cm of arterial length.

In rats of the control group without angioplasty, carotid artery smooth muscle cells yielded 7.7±1.2 $\mu$g DNA/cm. In the angioplasty-control rats, restenosis was seen and the yield of DNA from carotid artery smooth muscle cells was 19.9±1.8 $\mu$g/cm. In the test rats, recipients after balloon-mediated injury of 250 mg/kg AS2-1 twice daily for 14 d, carotid artery smooth muscle cells yielded 17.0±2.0 $\mu$g DNA/cm, corresponding to an inhibition of DNA synthesis relative to the angioplasty-controls of 23.8%.

The inhibition of DNA synthesis in carotid artery smooth muscle cells of AS2-1-treated rats relative to the angioplasty-control rats is further correlated with observations of the extent of restenosis. These observations emphasize that AS2-1 is useful in treating or preventing smooth muscle cell proliferation in restenosis in vivo.

EXAMPLE 3

Reduction of the ratio of neointimal smooth muscle cells to medial smooth muscle cells in rat carotid artery in vivo In addition to the indirect measurement of inhibition of restenosis by the inhibition of DNA synthesis, the inhibition of restenosis in the rat model described in Example 2 above was measured directly as a ratio of neointimal smooth muscle cells (new smooth muscle cells in the intimal layer nearest the lumen of the artery; neointimal cells grow into the lumen and thus represent restenosis) to medial smooth muscle cells (smooth muscle cells in the layer radially outward of the intimal layer; medial cells do not proliferate in restenosis). This experiment also examined whether pretreatment with phenylacetic acid or related compounds could prevent or inhibit restenosis.

Rats used and carotid artery injury techniques were as described in Example 2. Compositions of AS2-1 were as described in Example 2, except that an additional formulation of 200 mg/kg was prepared and used. Rats were divided into three groups. Group (1) were controls which received balloon angioplasty on day 0 of the 15-d trial and no AS2-1. Group (2) received 250 mg/kg of AS2-1 twice daily on days 0–3 and 200 mg/kg of AS2-1 twice daily on days 5–15. Angioplasty was performed on Group (2) animals on day 2 of the trial. Group (3) received 250 mg/kg of AS2-1 twice daily on days 0–4 and 200 mg/kg of AS2-1 twice daily on days 6–15, with angioplasty performed on day 0 of the trial. Each group contained five animals.

On day 15, the animals were sacrificed and sections of carotid artery dissected. Areas of smooth muscle cells jutting into the lumen were excised and weighed or the cells counted. The layer of smooth muscle cells lying radially outward from the intimal layer was also dissected and weighed or cells counted. The average weights or cell counts were then used to determine the ratio of neointimal to medial cells. These ratios were calculated for all three groups.

Group (1) had a mean neointimal/medial ratio of 1.28±0.209. Group (2) had a mean neointimal/medial ratio of 0.85±0.152. Group (3) had a mean neointimal/medial ratio of 0.71±0.125. There have been statistically significant differences between Group (1) and Group (2) (P<0.01) and between Group (1) and Group (3) (P<0.001).

These results indicate that treatment with AS2-1, commencing either before or after an angioplasty, is effective in inhibiting proliferation of smooth muscle cells and subsequent restenosis.

All of the compositions and methods disclosed and claimed herein can be made and executed without undue experimentation in light of the present disclosure. While the compositions and methods of this invention have been described in terms of preferred embodiments, it will be apparent to those of skill in the art that variations can be applied to the compositions and methods and in the steps or in the sequence of steps of the method described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for the treatment or inhibition of restenosis, comprising:
   administering to a patient a composition comprising an effective amount of phenylacetic acid, a salt thereof, or an analog thereof, wherein said analog is phenylacetylglutamine, iso-phenylacetylglutamine or of the formula:

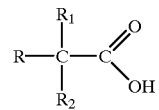

wherein R is selected from the group consisting H and $C_3H_7$; $R_1$ is selected from the group consisting of H, $CH_3$, $CH_3$—O—, $C_2H_5$, and $C_3H_7$; and $R_2$ is selected from the group consisting of:

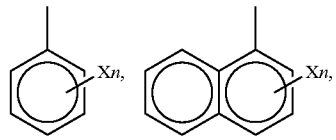

wherein X is selected from the group consisting of $CH_3$, Cl, F, and —OH; and n is 0, 1, 2, 3, or 4.

2. The method of claim 1, wherein said composition further comprises at least one pharmaceutically-acceptable carrier, diluent, or excipient.

3. The method of claim 1, wherein said composition comprises an effective amount of two or more compounds, each of said compounds selected from the group consisting of phenylacetic acid, pharmaceutically-acceptable salts thereof, pharmaceutically-acceptable precursors thereof, and pharmaceutically-acceptable analogs thereof.

4. The method of claim 3, wherein said compounds are phenylacetylglutamine and phenylacetic acid or pharmaceutically acceptable salts thereof.

5. The method of claim 4, wherein said phenylacetylglutamine and phenylacetic acid are present in a 1:4 ratio.

6. The method of claim 4, wherein the phenylacetylglutamine is L-phenylacetylglutamine.

7. The method of claim 3, wherein said compounds are phenylacetylglutamine and iso-phenylacetylglutamine.

8. The method of claim 6, wherein the molar ratio of phenylacetylglutamine to iso-phenylacetylglutamine is 4 to 1.

9. The method of claim 3, wherein said compounds are L-phenylacetylglutamine and L-iso-phenylacetylglutamine.

* * * * *